(12) United States Patent
Hewson et al.

(10) Patent No.: US 6,435,180 B1
(45) Date of Patent: Aug. 20, 2002

(54) METHOD AND APPARATUS FOR DELIVERING HUMIDIFIED AIR TO A FACE MASK

(75) Inventors: C. Bruce Hewson, West Vancouver; Benjamin I. Wiens, Coquitlam; James B. Wong, Port Moody, all of (CA)

(73) Assignee: J&M Distributors Limited, British Columbia (CA)

( * ) Notice: Subject to any disclaimer, the term of this patent is extended or adjusted under 35 U.S.C. 154(b) by 0 days.

(21) Appl. No.: 09/558,931

(22) Filed: Apr. 26, 2000

Related U.S. Application Data

(63) Continuation-in-part of application No. 09/345,417, filed on Jul. 1, 1999, now abandoned.

(51) Int. Cl.[7] .............................................. A61M 16/00
(52) U.S. Cl. .............................. 128/204.18; 128/203.12
(58) Field of Search ........................ 128/203.17, 203.16, 128/203.12, 203.26, 203.27, 204.14, 204.13, 204.17, 203.25, 204.18, 200.21, 200.14, 200.18; 239/338; 261/DIG. 65, 154

(56) References Cited

U.S. PATENT DOCUMENTS

| | | | |
|---|---|---|---|
| 3,638,926 A | 2/1972 | Melville et al. | 261/130 |
| 3,659,604 A | 5/1972 | Melville et al. | 128/212 |
| 3,894,537 A | 7/1975 | Camp | 128/193 |
| 3,923,057 A | 12/1975 | Chalon | 128/188 |
| 4,010,748 A | 3/1977 | Dobritz | 128/192 |
| 4,014,382 A | 3/1977 | Heath | 165/60 |
| 4,028,444 A | * 6/1977 | Brown et al. | 128/203.26 |
| 4,038,519 A | 7/1977 | Foucras | 219/301 |
| 4,121,583 A | 10/1978 | Chen | 128/192 |
| 4,164,220 A | 8/1979 | Brickell et al. | 128/185 |
| 4,200,093 A | 4/1980 | Camp | 128/200.14 |
| 4,203,027 A | 5/1980 | O'Hare et al. | 219/275 |
| 4,355,636 A | 10/1982 | Oetjen et al. | 128/203.27 |
| 4,401,114 A | 8/1983 | Lwoff et al. | 128/200.14 |

(List continued on next page.)

*Primary Examiner*—John G. Weiss
*Assistant Examiner*—Teena Mitchell
(74) *Attorney, Agent, or Firm*—Oyen Wiggs Green & Mutala

(57) ABSTRACT

A pass-over humidifier for delivering a supply of heated, humidified air through an elongated conduit to a mask worn by a patient. The humidifier is designed for wear by a patient during sleep to treat chronic breathing disorders such as allergic rhinitis. A supply of air is drawn into a humidification chamber by a fan and is passed over the surface of a water reservoir where it picks up moisture. The moisture-laden air is mixed with a stream of relatively dry heated air within the humidifier to form a humidified air stream. The humidified air stream is discharged from the humidifier into the elongate conduit at a temperature within the range of approximately 45–57° C. and at a relative humidity within the range of approximately 25–55%. Since the humidified air is preferably heated to a temperature exceeding 45° C., the humidifier is essentially self-sterilizing. The temperature of the humidified air stream drops significantly as it passes tough the conduit between the humidifier and the mask. By the time the air stream has reached the mask the temperature is preferably within the range of 30–35° (i.e. slightly less than body temperature) and the relative humidity has increased to approximately 90–100%. The humidifier is configured such that temperature drop over the length of the conduit does not result in condensation of water vapor within the conduit upstream from the mask.

23 Claims, 10 Drawing Sheets

U.S. PATENT DOCUMENTS

| | | | |
|---|---|---|---|
| 4,621,632 A | 11/1986 | Bartels et al. | 128/203.27 |
| 4,643,183 A | 2/1987 | Seilinger | 128/205.17 |
| 4,667,084 A | 5/1987 | Regge | 219/301 |
| 4,686,354 A | 8/1987 | Makin | 219/301 |
| 4,693,324 A | 9/1987 | Choiniere et al. | 174/147 |
| 4,708,831 A | 11/1987 | Elsworth et al. | 261/130 |
| 4,776,990 A | 10/1988 | Verity | 261/128 |
| 4,784,131 A | 11/1988 | Schroeder | 128/206.16 |
| 4,798,230 A | 1/1989 | Hopperdietzel | 138/103 |
| 4,829,998 A | 5/1989 | Jackson | 128/203.12 |
| 4,953,546 A | 9/1990 | Blackmer et al. | 128/203.16 |
| 5,062,145 A | 10/1991 | Zwaan et al. | 392/396 |
| 5,086,766 A | 2/1992 | Beacham | 128/203.27 |
| 5,163,423 A | 11/1992 | Suzuki | 128/203.26 |
| 5,195,527 A | 3/1993 | Hicks | 128/205.12 |
| 5,226,411 A | 7/1993 | Levine | 128/203.26 |
| 5,367,604 A | 11/1994 | Murray | 392/394 |
| 5,377,670 A | 1/1995 | Smith | 128/204.17 |
| 5,381,511 A | 1/1995 | Bahar et al. | 392/472 |
| 5,454,061 A | 9/1995 | Carlson | 392/478 |
| 5,529,060 A | 6/1996 | Salmon et al. | 128/203.16 |
| 5,558,084 A | 9/1996 | Daniell et al. | 128/203.17 |
| 5,588,423 A | 12/1996 | Smith | 128/203.26 |
| 5,640,951 A | 6/1997 | Huddart et al. | 128/204.77 |

\* cited by examiner

METHOD AND APPARATUS FOR DELIVERING HUMIDIFIED AIR TO A FACE MASK

This application is a continuation-in-part of application serial No. 09/345,417 filed Jul. 1, 1999, which is currently abandoned.

TECHNICAL FIELD

This application relates to a humidifier for delivering a supply of heated, humidified air through an elongated conduit to a mask worn by a patient. The humidifier is designed for use by a patient during sleep to treat chronic breathing disorders such as allergic rhinitis. The relative humidity of the air stream is regulated to ensure that it will not condense to form water droplets within the interior of the conduit.

BACKGROUND

The air passageways in patients suffering from chronic breathing disorders, such as asthma, rhinitis, bronchitis, sinusitis and the like, are often in a persistent post-traumatically inflamed state. The Applicant has determined that one method of effectively treating such conditions is to supply heated, pollutant-free, humidified air to the patient at night while he or she is sleeping. This enables the patient's air passageways to rest and partially recover from the inflammation. The patient is then able to resume a normal life during waking hours.

Conventional portable humidifiers designed for home use do not Significantly alter the humidity of the room that they are operating in and are therefore of limited benefit. Moreover, to the extent that such portable humidifiers do increase ambient humidity, they result in undesirable side effects. For example, increased ambient humidity levels may exacerbate rather than alleviate a patient's respiratory tract inflammation by causing increased growth of mites, fungi or other allergens in the patient's sleeping environment.

Breathing tents surrounding all or a portion of the patient's bed for delivering heated, humidified air to the patient during sleep are also well-known in the prior art. However, such tents are not desirable since they often result in overheating of the patient and cause excess perspiration.

A more effective means for raising the humidity of air inhaled by a patient at rest is to deliver humidified air directly to a face mask worn by the patient. Typically, the mask is connected to a bedside humidifier apparatus by an elongate conduit. One problem which has arisen with such devices is the tendency for the humidified air to condense as water vapour within the conduit. The water vapour then drips into the face mask, repeatedly rousing the patient from sleep.

Relative humidity is a percentage expression of the actual water vapour content of a gas as compared to its capacity to carry water at any given temperature. The capacity of a gas to hold water in its vaporous state increases with molecular velocity as the temperature of the gas rises. For example, as the temperature of air drops, its capacity to hold moisture also declines proportionately and hence the relative humidity increases. When the air temperature drops below the dew point, the excess vapour condenses as water droplets. Condensation of water vapour or "condensate rainout" can result from a drop in the temperature of humidified air as it passes through a conduit, such as a conduit extending between a supply of humidified air and a face mask.

One approach for addressing this problem is to uniformly heat the air travelling through the conduit by means of electric wires wound around the conduit and controlled by a temperature sensor. For example, U.S. Pat. No. 3,638,926 describes a humidification system wherein the tube interconnecting the humidifier and the patient is heated at least partially along its length by means of electric elements embedded within the wall of the tube. The primary drawback of heated wire systems is expense. Heated wire systems, such as those used in hospitals, tend to be about twice as expensive as conventional humidifiers.

Another approach for controlling water vapour condensation is to raise the temperature of the humidified air introduced into the conduit inlet to a temperature above the preferred outlet temperature. The inlet temperature is calibrated to take into account the anticipated heat drop along the length of the conduit and the corresponding increase in relative humidity. For example, in the '926 patent referred to above, the air leaving the humidifier is preferably at 35.5° C. (i.e. approximately body temperature) and is between 85–100% saturated. The air temperature is then increased to 47.8° C. to compensate for an anticipated temperature drop of about 10° C. along the length of the delivery hose. This avoids condensation of water vapour between the humidifier and the mask worn by the patient.

One drawback of the '926 system described above is that the humidified air is not heated and maintained at a temperature sufficient to sterilize the air supply to kill all air-borne bacteria or viruses before delivery to the patient. Moreover, the '926 system is reliant upon the use of supplementary heated wires in the delivery hose to reduce the magnitude of the heat drop.

U.S. Pat. No. 5,558,084, Daniell et al., describes a humidifier having a delivery tube for providing humidified gases to an intubated patient or a face mask worn by a patient. The Daniell et al. humidifier includes temperature sensors for sensing the ambient temperature and the temperature of gas expelled from the humidifier. Electronic control circuitry is provided for adjusting the temperature of the expelled gas depending upon the ambient temperature to minimize condensate rainout in the air delivery tube extending between the humidifier and the face mask. The Daniell et al. humidifier does not include an internal gas supply but rather is designed to connect to a CPAP machine or some other external gas supply. This limits the suitability of the Daniell et al. invention for home use in the treatment of sinusitis and other similar disorders where a large flow rate of humidified gas is not required but where it is important that the air be delivered at consistently high relative humidity. The Daniell et al. invention does not teach the advantages of mixing separate streams of hot humidified air and hot dry air together within the humidifier to achieve a mixed air stream which is discharged from the humidifier by a fan blower at the optimum temperature and relative humidity.

The need has therefore arisen for a humidification system which delivers substantially sterile air to a patient for inhalation during sleep in a cost-effective manner. The air is delivered at a preferred temperature and humidity to avoid the disadvantages of vapour condensation within the air delivery conduit.

SUMMARY OF INVENTION

In accordance with the invention, an apparatus and method for delivering humidified air through a conduit to a patient for inhalation during sleep is disclosed. The conduit has an inlet connected to a humidifier and an outlet connected to a breathing mask worn by the patient.

The applicant's apparatus comprises a humidifier having an inlet for receiving a supply of intake air; a first chamber for holding a first volume of the intake air; a second chamber for holding a second volume of the intake air, wherein the second volume of air is passed over the surface of water contained within the second chamber; a heater for heating the water and the second volume of air within the second chamber; a mixing conduit for receiving and mixing together separate first and second streams of air discharged from the first and second chambers respectively; and an adjustable regulator for regulating the amount of the second stream of air passing into the mixing conduit.

Preferably the second chamber is located within the first chamber and the first chamber surrounds the second chamber. The heater is disposed so that it also heats the first volume of air in the first chamber. Advantageously, the first and second air streams are heated to approximately the same temperature. The second container may consist of a container and a removable lid for covering the container, wherein the intake air passes from the first chamber into the second chamber through an opening defined between the container and the lid.

The humidifier preferably includes a first compartment and a second compartment, wherein the first and second chambers are located in the first compartment and wherein the mixing conduit extends from the first compartment into the second compartment. The humidifier also includes an air outlet port connectable to the face mask and a fan mounted in the second compartment for conveying air from the mixing conduit to the air outlet port. Preferably, the first compartment is located above the second compartment and the heater is disposed in a lower portion of the first compartment.

The air inlet consists of a inlet conduit extending through the second compartment into the first compartment. The inlet conduit has an open upper end to discharge the intake air into the first chamber. The second chamber is located between the inlet conduit and the mixing conduit. The inlet conduit and mixing conduit are preferably disposed on opposite sides of the humidifier.

The mixing conduit comprises a first tube having an open upper end in communication with the first chamber and a second tube having an upper portion in communication with the second chamber and a lower portion extending within the first tube. The adjustable regulator comprises a valve for regulating flow of the second air stream into the second tube.

The applicant has also developed a method for delivering humidified air through an unheated conduit to a patient, the conduit having an inlet connected to a humidifier and an outlet connected to a breathing mask worn by the patient. The applicant's method comprises the steps of:
  (a) heating a first volume of air in the humidifier to form a supply of heated dry air;
  (b) heating a volume of water in the humidifier and passing a second volume of air over the surface of the water to form a supply of heated moisture-laden air;
  (c) adjustably mixing the heated dry air and the moisture-laden air together in the humidifier to form a stream of heated humidified air;
  (d) conveying the heated humidified air from the humidifier through the conduit to the mask,
wherein the temperature and relative humidity of the humidified air is adjusted to substantially prevent condensation of the humidified air in the conduit.

Preferably, the temperature of the humidified air while resident within the conduit decreases to less than 40° C. and the relative humidity of the humidified air while resident within the conduit increases to greater than 80%.

In an alternative embodiment of the invention, the separate streams of heated dry air and heated moisture-laden air may be mixed in fixed amounts in the mixing conduit and the adjustable regulator may be omitted. The mixing conduit may extend into an upper portion of the first chamber for drawing dry air into the mixing conduit at a relatively high temperature.

A method of treating inflammation of the mucous membranes of the upper respiratory tract of a patient is also disclosed. The method may be used, for example, in the treatment of conditions such as vasomotor rhinitis, seasonal allergic rhinitis, perennial rhinitis and post-influenza cough syndrome. The method comprises the steps of:
  (a) providing a portable humidifier apparatus, the apparatus comprising a source of heated humidified air, a face mask and an air delivery tube for delivering the heated humidified air from the humidifier to the face mask;
  (b) fitting the face mask over at least the nose of the patient; and
  (c) delivering the humidified air from the humidifier to the face mask for a prolonged period of time while the patient is at rest, wherein the humidified air at the face mask is at a temperature within the range of 25–35° C. and at a relative humidity exceeding 90%.

BRIEF DESCRIPTION OF DRAWINGS

In drawings which describe embodiments of the invention but which should not be construed as restricting the spirit or scope of the invention in any way.

DETAILED DESCRIPTION OF THE PREFERRED EMBODIMENTS

Figure 1:
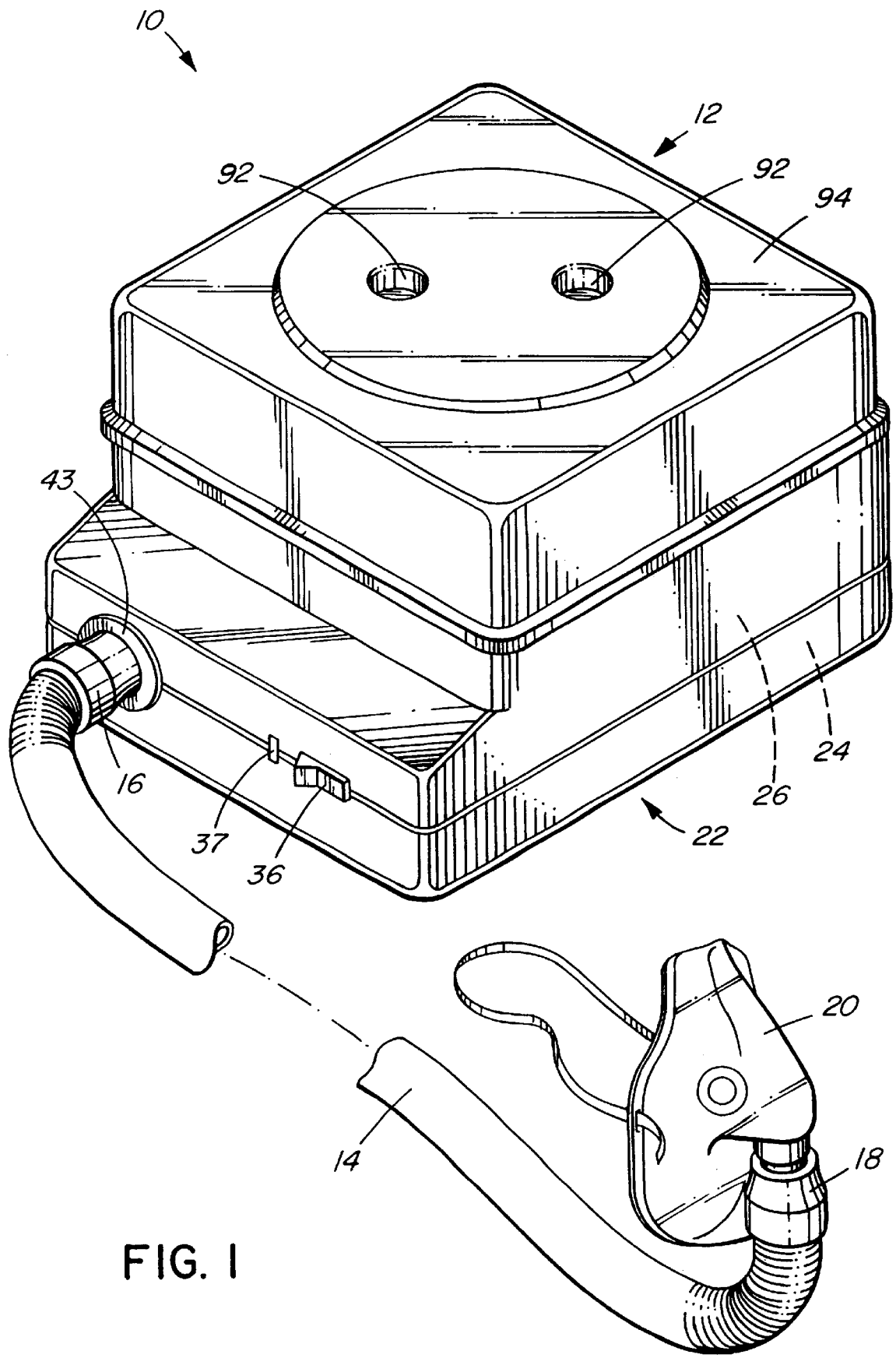
FIG. 1 is an isometric view of the applicant's invention showing the humidifier, air delivery conduit and face mask interconnected.

FIG. 1 illustrates an apparatus 10 for delivering heated, humidified air to a patient at a controlled rate for inhalation during sleep. Apparatus 10 includes a humidifier 12 for providing a supply of humidified air; a mask 20 for wear by the patient; and an elongate conduit 14 having an inlet 16 connectable to humidifier 12 and an outlet 18 connectable to mask 20. The invention is configured to prevent condensation of water vapour within conduit 14.

Figure 2:
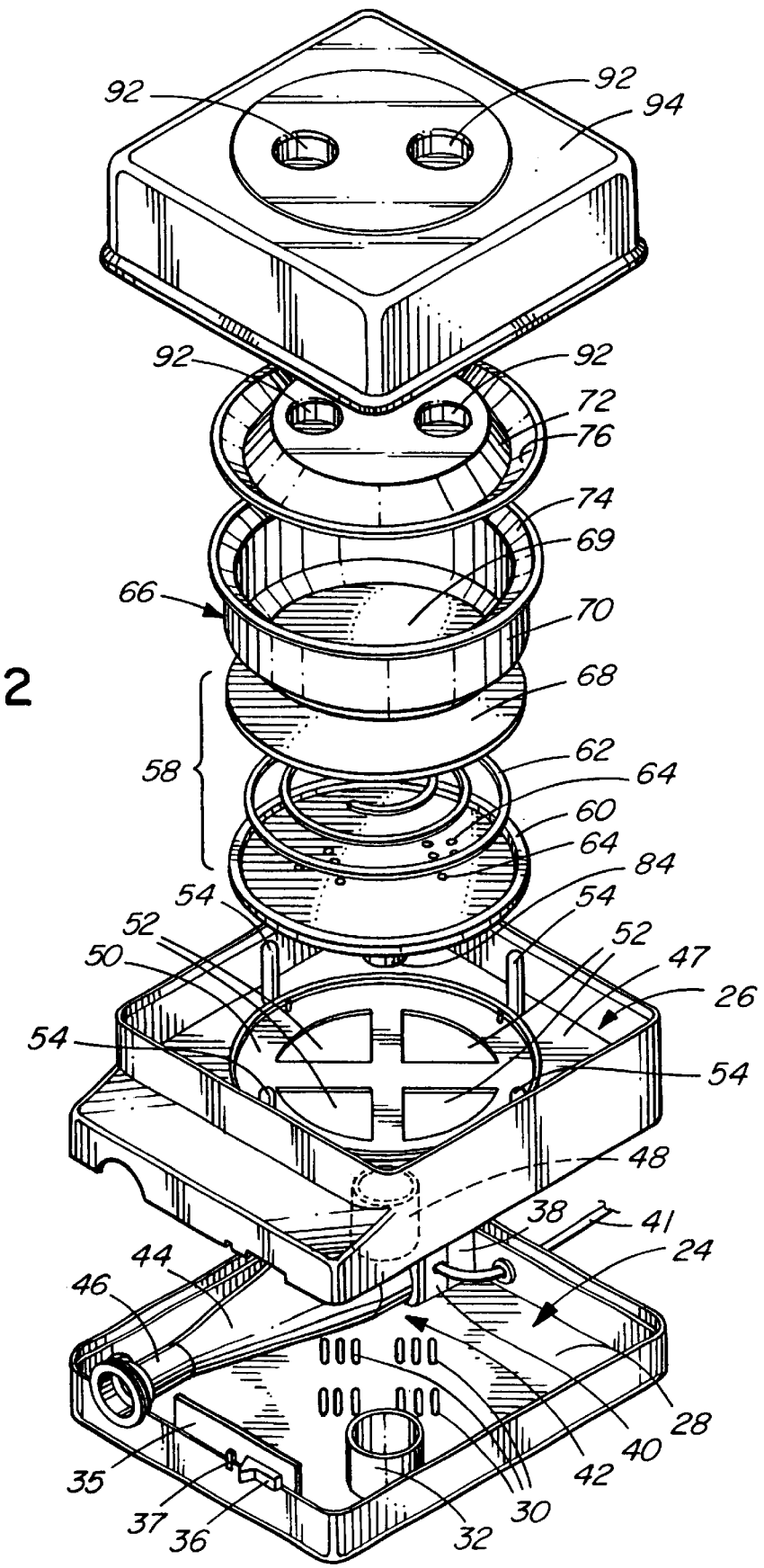
FIG. 2 is an exploded isometric view of the applicant's humidifier.
Figure 3:
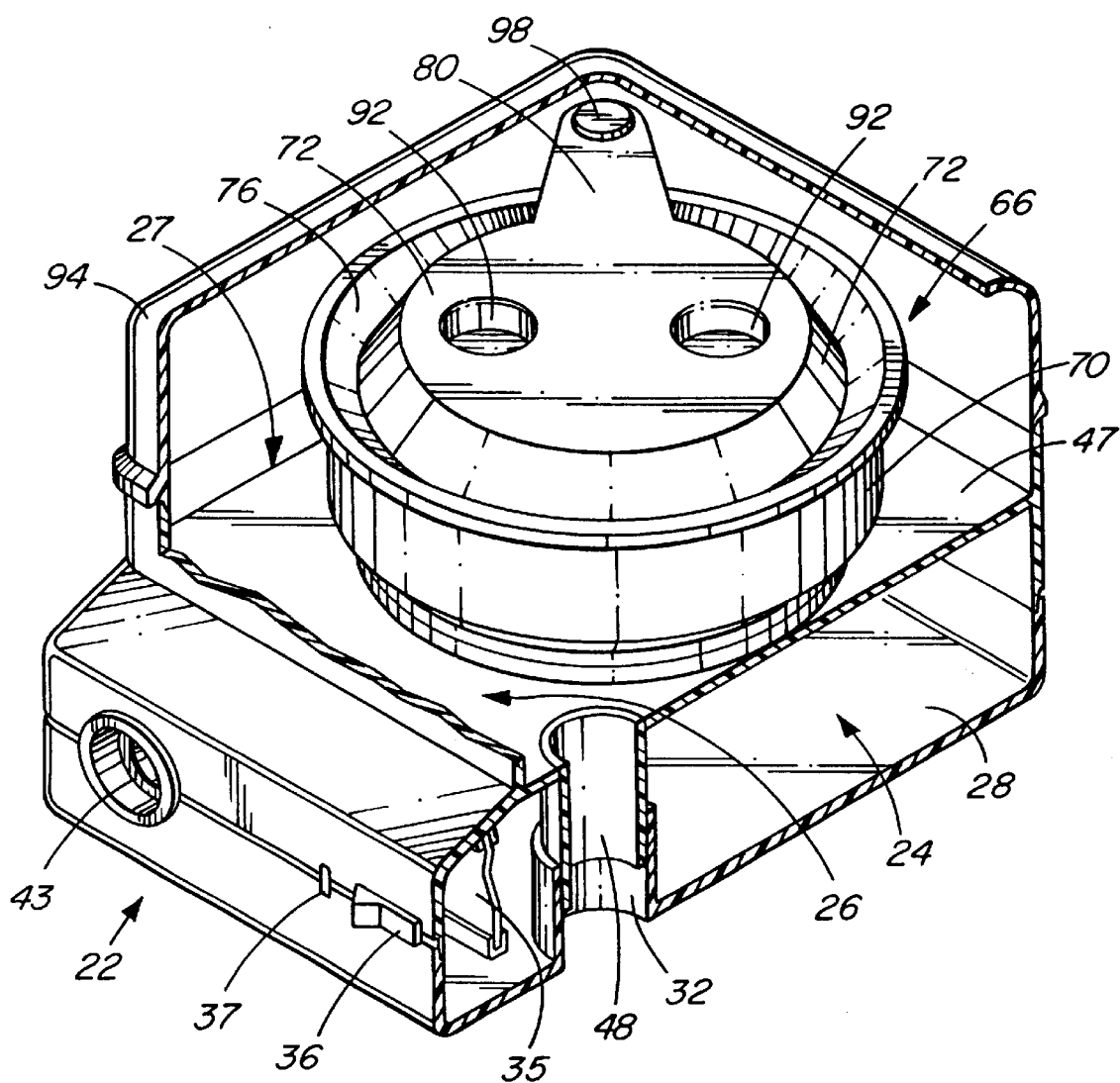
FIG. 3 is a front isometric fragmented view of the applicant's humidifier.
Figure 4:
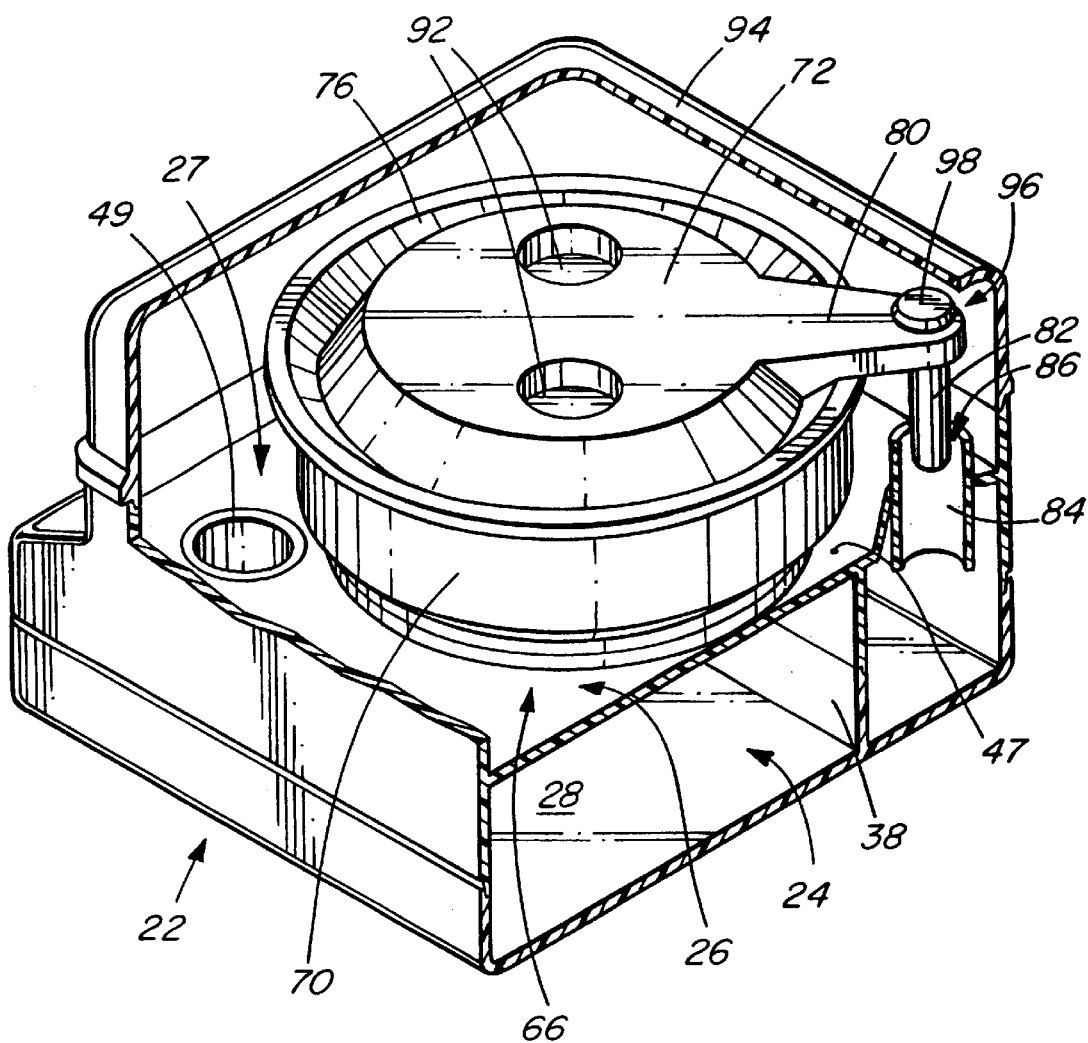
FIG. 4 is a rear isometric fragmented view of the applicant's humidifier.
Figure 5:
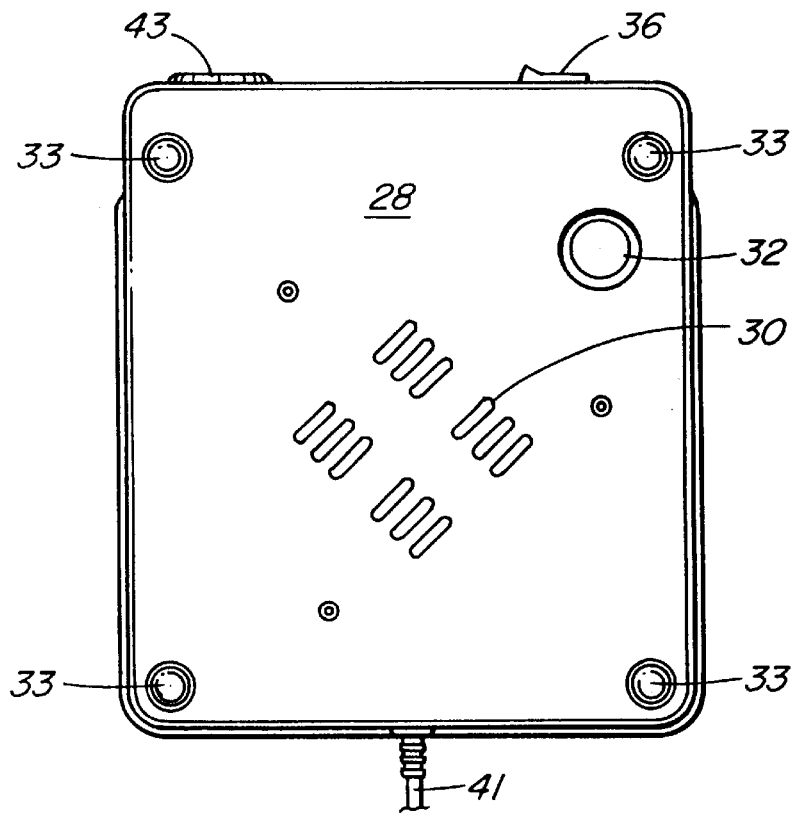
FIG. 5 is a bottom plan view of the applicant's humidifier.
Figure 6:
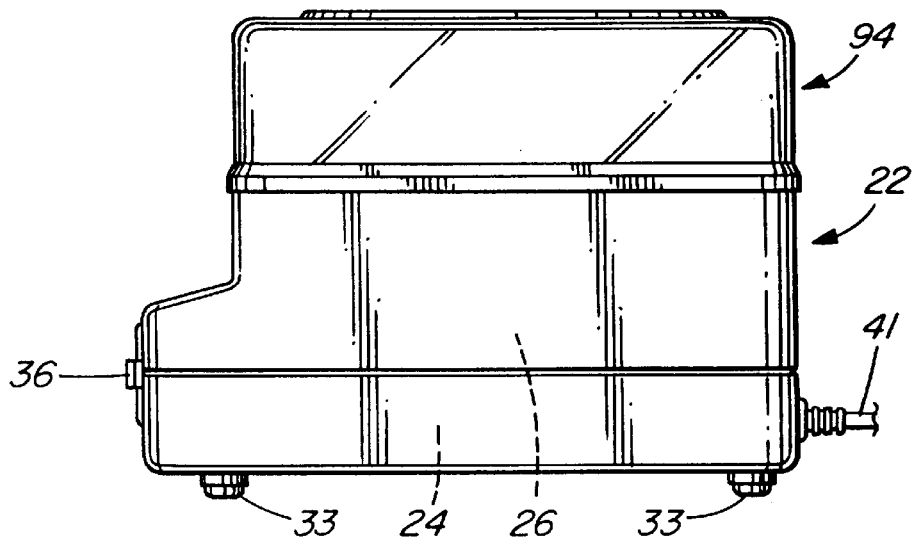
FIG. 6 is a side elevation of the applicant's humidifier in its assembled configuration.
Figure 7:
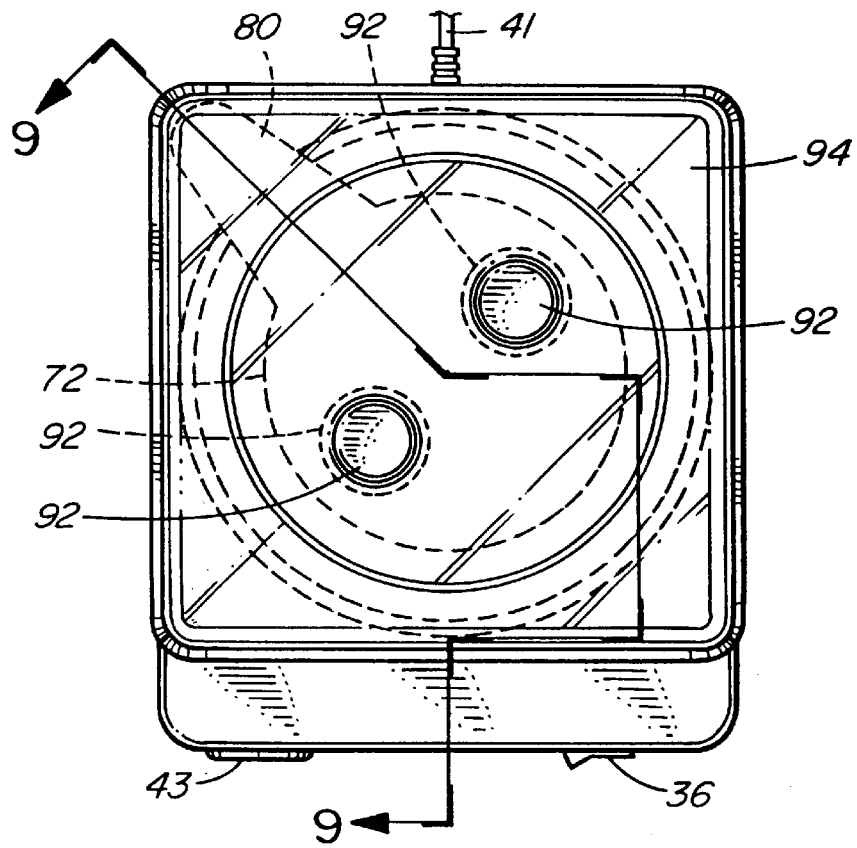
FIG. 7 is a top plan view the applicant's humidifier showing he outline of the water container and lid in phantom outline.
Figure 8:
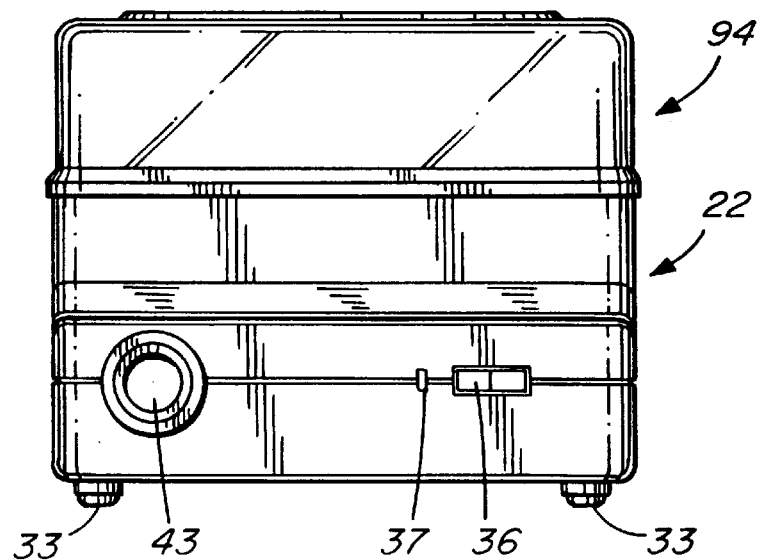
FIG. 8 is a front elevational view of the applicant's humidifier.

As shown best in FIGS. 2–4, humidifier 12 includes a housing 22 comprising a lower compartment 24 and an upper compartment 26. Lower compartment 24 includes a bottom panel 28 having a central grille 30 and an air inlet 32 formed therein. Bottom panel 28 is supported a short distance above a support surface by feet 33 (FIGS. 5 and 6).

An electric fan is mounted within lower compartment 24 and is controlled by a switch 36 connected to a front electronics panel 35 of lower compartment 24. Fan 40 is connectable to a power supply by a cord 41. An on/off indicator light 37 is also connected to panel 35 adjacent to switch 36.

Figure 10:
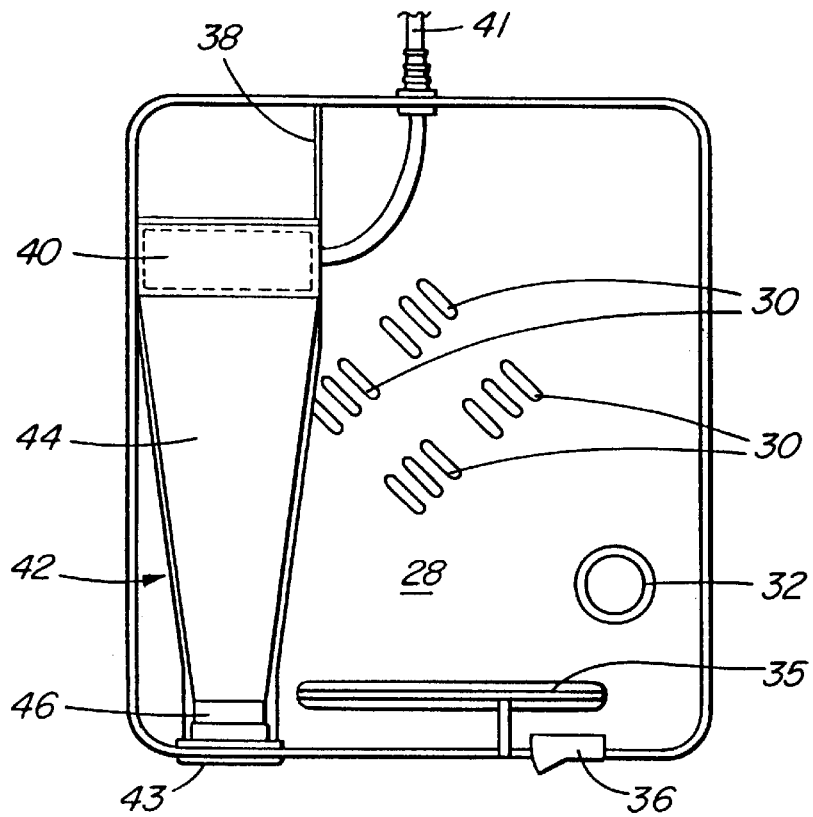
FIG. 10 is a top plan view of a bottom compartment of the applicant's humidifier housing an electric fan for blowing humidified air through an exhaust conduit to an air outlet.

An air exhaust conduit 42 is mounted adjacent to fan 40 within lower compartment 24 (FIG. 10). Exhaust conduit 42 has a generally conical body 44 which tapers to a narrow end 46 for discharging humidified air through an outlet 43 into conduit 14 (FIG. 1). Fan 40 is preferably a relatively quiet blade fan although any suitable fan capable of drawing intake air through inlet 32 and expelling humidified air through exhaust conduit 42 could be substituted. As described further below, lower compartment 24 includes a baffle 38 for ensuring that humidified air flowing downwardly into lower compartment 24 is drawn into fan 40 and is expelled into exhaust conduit 42 (FIGS. 4 and 10).

The upper compartment 26 of housing 22 rests on a narrow ledge formed on the perimeter of lower compartment 24. As shown best in FIGS. 2 and 3, upper compartment 26 includes a bottom panel 47 and an air intake conduit 48 which is alignable with air inlet 32. Conduit 48 has an open upper end 49 in communication with upper compartment 26. Thus, fresh intake air drawn into humidifier 12 may pass through air inlet 32 and conduit 48 for delivery to the interior of upper compartment 26.

A circular support 50 having a plurality of apertures 52 formed therein is provided in a central portion of upper compartment 26 (FIG. 2). A plurality of alignment posts 54 are spaced around the perimeter of support 50 to assist in aligning a water container 66 as discussed further below.

A heating element 58 comprising a lower panel 60, a heating coil 62 and an upper panel 68 is positionable on support 50. Lower panel 60 has apertures 64 formed therein for ventilation purposes to permit some heat to escape downwardly through apertures 52 into housing lower compartment 24. This enables some pre-heating of the intake air passing through air inlet 32 within housing lower compartment 24. The temperature in lower compartment 24 is, however, not increased to a significant degree to avoid overheating of the fan motor.

A water container 66 comprising a bottom panel 69, a cylindrical sidewall 70 and a removable lid 72 is removably positionable on heating element 58 within housing upper compartment 26. Container sidewall 70 includes a flanged rim 74 extending around its perimeter. As shown best in FIG. 9, lid 70 has a mating rim 76 having a plurality of spaced ribs 78 formed thereon. When lid 72 is placed on container sidewall 70, ribs 78 maintain small vent(s) therebetween to permit the entry of intake air into container 66. The number, size and position of such vents may vary without departing from the invention.

Figure 9:
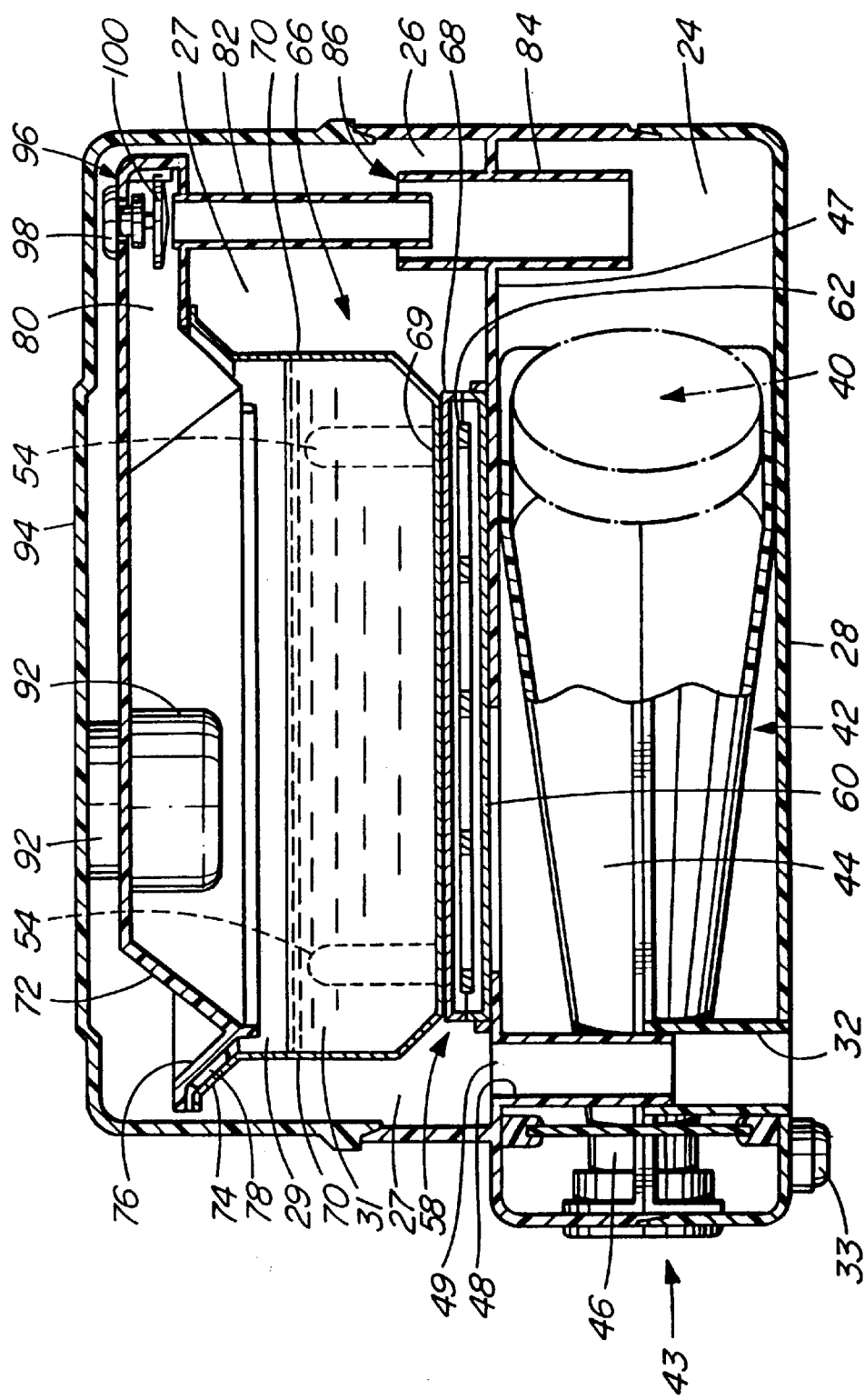
FIG. 9 is a sectional view of the applicant's humidifier taken along section line 9—9 of FIG. 7 and looking in the direction of the arrows.

Container 66 essentially defines two discrete air chambers within upper compartment 26, namely a first chamber 27 surrounding container 66 (FIG. 4) and a second chamber 29 within the interior of container 66 between the surface of the heated water 31 and the overlying lid 72 (FIG. 9). Accordingly, intake air drawn into humidifier 12 through the open end 49 of conduit 48 is either heated in the first chamber 27 surrounding container 66 or it passes into second chamber 29 as discussed above where it passes over the surface of the heated water 31 gathering moisture (FIG. 9). Preferably the temperature of the relatively dry air in first chamber 27 and the moisture-laden air in second chamber 29 is approximately the same (due to uniform heating of upper compartment 26 by heating element 58). First and second chambers are preferably heated to a temperature within the range of 65–80° C.

As shown best in FIG. 2, removable container lid 72 includes a pair of spaced-apart depressions 92 which serve as finger and thumb holds for lifting lid 72 clear of container 66. Housing 22 similarly includes a removable cover 94 having spaced-apart depressions 92 which may register with the depressions in lid 72 (FIG. 9) when humidifier 12 is assembled. As shown in FIG. 9, cover 94 rests on the upper edges of upper compartment 26 to enclose air chamber 27.

As shown best in FIGS. 4 and 9, container lid 72 includes a lateral extension 80 which discharges the moisture-laden air from container 66 into a downtube 82, which is in turn in communication with a mixing conduit 84. Conduit 84 extends between upper and lower compartments 24,26 through panel 47 and includes an open upper end 86 which receives the heated air from downtube 82. Thus, two separate streams of heated air are mixed together in mixing conduit 84 to form a humidified air stream, namely a first volume of relatively dry heated air from first chamber 27 and a second volume of relatively moisture-laden air from second chamber 29.

The rate and volume of moisture-laden air entering downtube 82 is regulated by a valve assembly 96 mounted at the end of lid lateral extension 80. As shown best in FIG. 11, valve assembly 96 comprises an adjustment knob 98 which is threadedly coupled to a valve 100. Adjustment knob 98 may be rotated to vary the degree of extension of valve 100 and hence the size of the opening leading into downtube 82. For example, when valve 100 is fully extended it covers the upper end of downtube 82 entirely, thereby preventing entry of moisture-laden air from second chamber 29 of container 66 into downtube 82.

The various components of humidifier 12 shown exploded apart in FIG. 2 are designed to fit compactly together without fasteners for ease of assembly and disassembly (for example, for cleaning purposes). In use, container 66 is partially filled with water 31 and humidifier 12 is assembled as shown in FIG. 2. The inlet end 16 of air delivery conduit 14 is plugged into outlet 43 of humidifier 12. The outlet end 18 of conduit 14 is connected to face mask 20 (FIG. 1).

The operation of humidifier 12 is activated by moving switch 36 to the "on" position after connecting cord 41 to an electrical power supply. This activates fan 40 and causes heating coil 62 to heat up. Coil 62 is preferably set to heat water 31 and the surrounding air within chambers 27, 29 of upper compartment 26 to a temperature within the range of 65–80° C. A temperature sensor (not shown) may be mounted near the discharge end of mixing conduit 84 for regulating the temperature of the discharged air stream and for preventing overheating of coil 62.

The operation of fan 40 causes heated air to be drawn down through conduit 84 from upper compartment 26 to lower compartment 24 where fan 40 is housed. This creates a partial vacuum in upper compartment 26 after lid 94 has been secured. As a result, fresh intake air is continuously drawn up through inlet 32 and intake conduit 48. The intake air is partially heated as it flows upwardly through inlet 32 and conduit 48 due to the operation of heating coil 62.

The intake air passes through the upper end 49 of conduit 48 into chamber 27 of upper compartment 26 (FIG. 4). Chamber 27 surrounds container 66. Some of the intake air is drawn into container 66 through small vent(s) defined between container rim 74 and the corresponding rim 76 of container lid 72 (FIG. 9).

The intake air which does not pass into container 66 is circulated within air chamber 27 where it increases in temperature before exiting downwardly into mixing conduit 84. The residence time of the air within chamber 27 is maximized by positioning mixing conduit 84 at a location opposite from the location of intake conduit 48.

Figure 11:
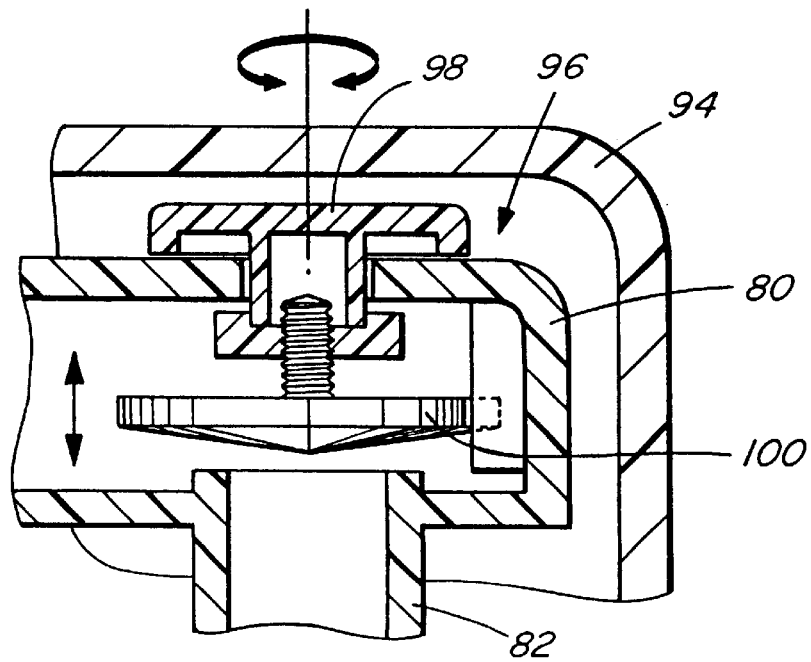
FIG. 11 is an enlarged, cross-sectional view of the adjustable regulator valve for regulating the volume of moisture-laden air entering the mixing conduit.

Humidifier 12 has a heated, "pass-over" design. That is, the intake air drawn into container 66 flows through air chamber 29 above the surface of heated water 31, causing the air to become moisture-laden (FIG. 9). After passing over water 31, the heated, moisture-laden air may be discharged into downtube 82. As discussed above, the volume of moisture laden air entering downtube 82 is regulated by valve assembly 96 mounted at the end of lid lateral extension 80. As shown in FIG. 11, valve assembly 96 may be manually adjusted by turning adjustment knob 98. Adjustment knob 98 is threadedly coupled to valve 100 which directly overlies the opening into downtube 82.

Preferably valve assembly 96 is set so that a relatively small amount of moisture-laden air flows trough downtube 82 into mixing conduit 84. The relatively dry air stream from air chamber 27 and the relatively moisture-laden air from air chamber 29 mix together in mixing conduit 84 to form a humidified air stream which is drawn downwardly into fan 40 located in lower compartment 24. Baffle 38 is positioned to ensure that substantially all of the downwardly flowing humidified air discharged from the lower end of mixing conduit 84 is drawn into fan 40 and is not dispersed into other portions of lower compartment 24 (FIG. 4).

Fan 40 blows the humidified air through exhaust conduit 42 and humidifier outlet 43 into conduit 14. Fan 40 is set to ensure a comfortable air flow rate through mask 20 (normally 15–20 litres per minute). Preferably, the temperature of the humidified air discharged from outlet 43 is within the range of 45–57° C. and has a relative humidity within the range of 25–55%.

Humidifier 12 is essentially self-sterilizing since live microorganisms are killed at temperatures above 45° for prolonged periods. A filter (not shown) may be mounted in air inlet 32 for filtering air-borne particles, such as pollen, dust or house mites.

Optionally, a supplementary temperature sensor (not shown) may be mounted at the narrow end 46 of exhaust conduit 42 to trigger shut-off of heating coil 62 if the temperature of the discharged humidified air stream rises above a safe level (i.e. above approximately 65°).

Conduit 14 preferably comprises smooth bore CPAP-type hose and is three to six feet in length. The temperature of the humidified air stream drops significantly as it passes through conduit 14 between humidifier 12 and mask 20. By the time the air stream has reached mask 20 the temperature is preferably within the range of 30–35° (i.e. slightly less than body temperature) and the relative humidity has increased to approximately 90–100%. The relative humidity of the air discharged from humidifier 12 can be easily adjusted depending upon the length of conduit 14 and the ambient room temperature by adjusting valve assembly 96. This is important to ensure that, whatever the operating conditions, the temperature drop over the length of conduit 14 does not result in condensation of water vapour within conduit 14 (i.e. upstream from mask 20).

Figure 12:
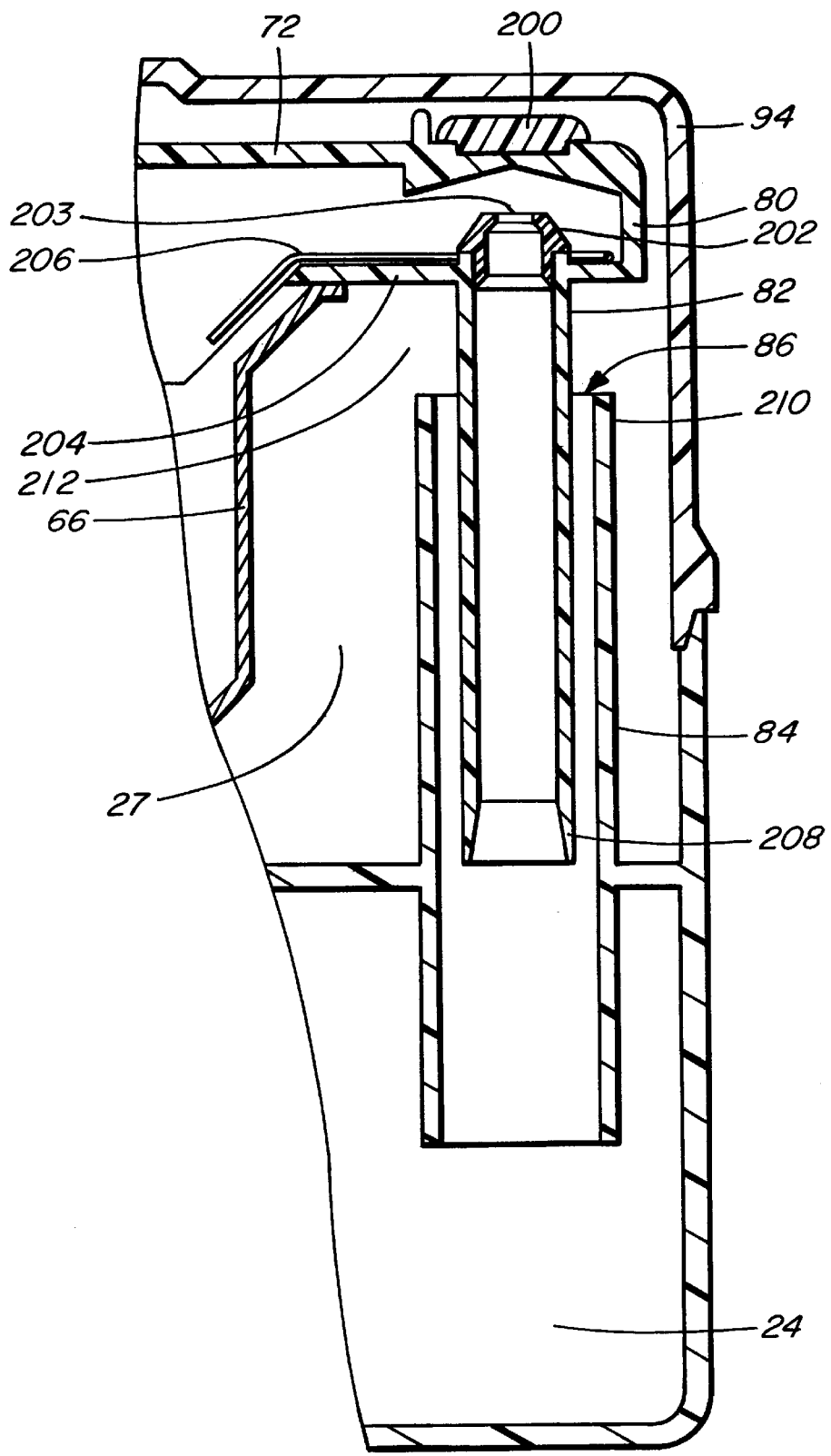
FIG. 12 is an enlarged, cross-sectional view of an alternative embodiment of the invention having a modified downtube and mixing conduit assembly and omitting the adjustable regulator valve.
Figure 13:
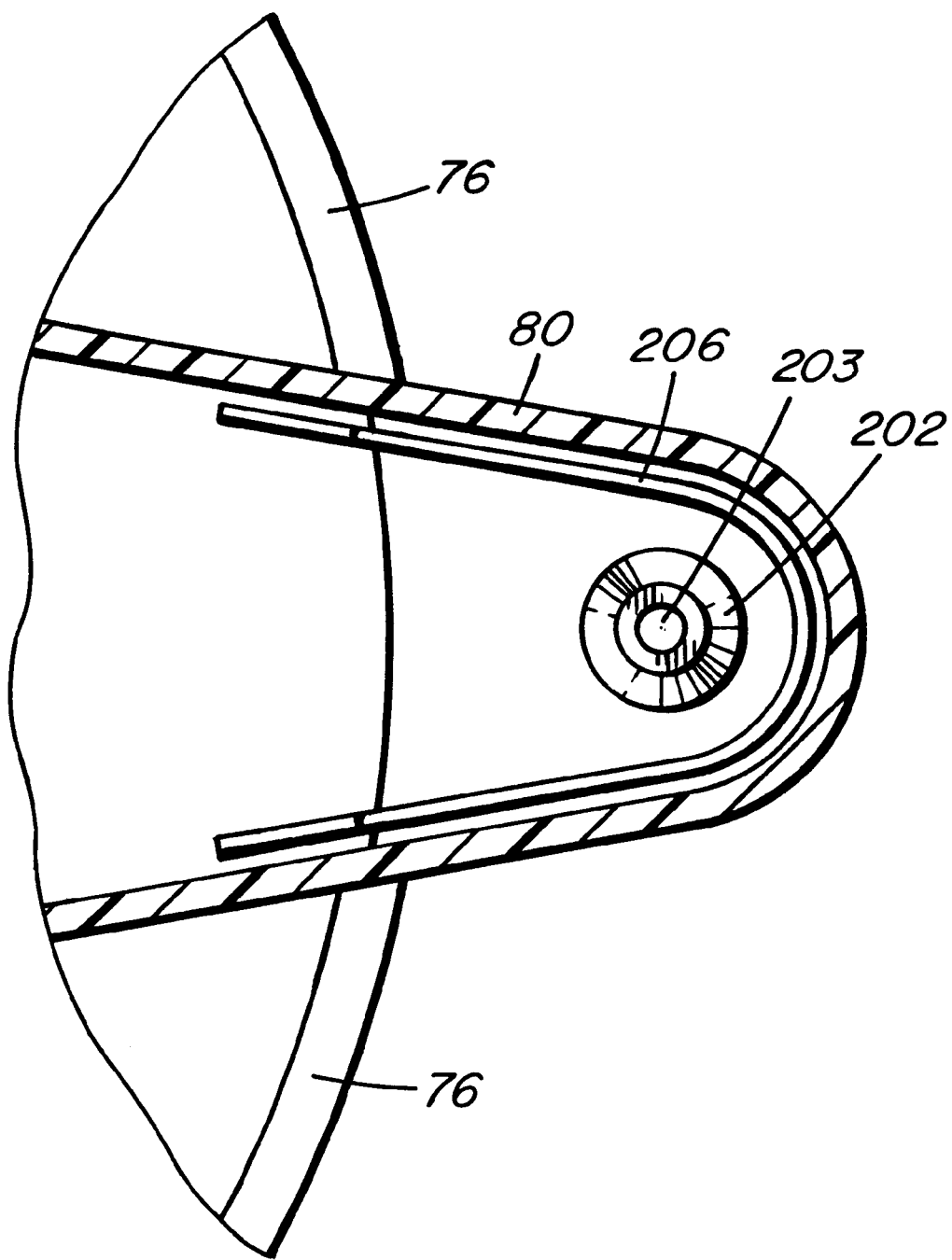
FIG. 13 is an enlarged top plan view of a portion of the embodiment of FIG. 12 showing a U-shaped wick surrounding an upper end of the downtube.

FIGS. 12 and 13 illustrate an alternative embodiment of the invention which does not include an adjustable valve assembly for regulating the amount of moisture-laden air flowing into downtube 82. In the embodiment of FIG. 12 the rotatable valve adjustment knob 98 of FIGS. 9 and 11 is replaced with a fixed button 200. A tapered inlet 202 having an opening 203 of a fixed diameter is provided at the upper end of downtube 82. Inlet 202 projects upwardly from base 204 of lid lateral extension 80. This reduces the likelihood that any water droplets condensing within extension 80, and accumulating on base 204, will pass into downtube 82 and into lower compartment 24 housing fan 40. The preferred orifice size of inlet opening 203 is approximately 3/16 to 1/4 of an inch (5.5 mm).

In this alternative embodiment of the invention a generally U-shaped wick 206 is provided for wicking any condensate from extension base 204 back into water container 66. Wick 206 is preferably a stainless steel wire which is removably mounted in lateral extension 80 by any suitable means. For example wick 206 may be held in place with small tabs or clips.

In the alternative embodiment of the invention shown in FIGS. 12 and 13 the outlet end 208 of downtube 82 is tapered outwardly. This helps prevent any condensate which passes into downtube 82 from forming a "water plug" at outlet end 208.

In the embodiment of FIGS. 12 and 13 the height of mixing conduit 84 has been increased in comparison to the first embodiment of FIG. 9. The upper end 210 of mixing conduit 84 therefore extends into an upper portion 212 of first chamber 27 surrounding water container 66. Dry air within first chamber 27 rises as it is heated. Consequently, the air contained in upper portion 210 of chamber 27 is at a relatively higher temperature than the air contained within lower portions thereof. By extending the height of mixing conduit 84 upwardly, relatively hotter dry air is drawn into mixing conduit 84 through opening 86 as compared to the embodiment of FIG. 9. This effectively reduces the relative humidity of the air blown from humidifier outlet 43 into conduit 14. In this embodiment of the invention, the relative humidity of the humidified air discharged from outlet 43 is preferably within the range of about 25–35%.

The Applicant's invention is useful in the treatment of chronic inflammation of the mucous membranes of a patient's upper respiratory tract. For example, in conditions such as vasomotor rhinitis, seasonal allergic rhinitis, perennial rhinitis and post-influenza cough syndrome, the mucous membranes of the affected patient become hypersensitive and inflamed. The purpose of the Applicant's invention is to passively treat such conditions by allowing the patient's sinuses and other respiratory tissue to remain in a resting state for a prolonged period of time. As used in this patent application "resting" means that the mucous membranes of the sinuses are not required to significantly alter the airflow through the patient's upper respiratory tract, such as by modulating the temperature or humidity of the air or by filtering air-borne particles. This is achieved by delivering air to the patient at very close to normal physiological conditions (i.e. at a mask temperature preferably within the range of approximately 30–33° C. and at a relative humidity exceeding 90%). The actual temperature at the mask is approximately 2–3 degrees higher due to some re-breathing of heated air at the mask. As indicated above, apparatus 10 preferably includes a filter for filtering air-borne particles.

In most cases it is expected patients would use the Applicant's invention at night during sleep for periods of about 5–8 hours per session. Typically about 3–20 sessions of treatment would be required to return the sinuses or other upper respiratory tract tissues to a non-hypersensitive state. Applicant's invention is not intended for long-term use although this may be desirable in some cases. Rather, in most cases, the invention would be used to reduce hypersensitivity during allergy seasons or following respiratory infections or periods of elevated air-borne pollutant levels.

During the treatment period the patient's sinuses should preferably be rinsed at intervals with isotonic saline solution to remove any pollutants which may present. This helps reduce the hypersensitivity of the respiratory tissue and ensures that the patient will achieve the full benefit of the passive humidified air therapy.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A humidifier comprising:
   (a) a first compartment and a second compartment;
   (b) an air inlet for receiving a supply of intake air;
   (c) a first chamber located in said first compartment for holding a first volume of the intake air;
   (d) a second chamber located in said first compartment for holding a volume of water and a second volume of the intake air, wherein the second volume of air is passed over the water contained within said second chamber;
   (e) a heater for heating the water and the first and second volumes of air;
   (f) a mixing conduit for receiving and mixing together separate first and second streams of air discharged from said first and second chambers respectively, wherein said mixing conduit extends from first compartment into said second compartment;
   (g) an air outlet connectable to a face mask; and
   (g) a fan mounted in said second compartment for conveying air from said mixing conduit to said air outlet.

2. The humidifier of claim 1, wherein said heater heats the first and second air streams to approximately the same temperature.

3. The humidifier of claim 1, wherein said second chamber comprises a container and a removable lid for covering said container, and wherein said intake air passes from said first chamber into said second chamber through an opening defined between said container and said lid.

4. The humidifier of claim 1, wherein said first compartment is located above said second compartment and wherein said heater is disposed in a lower portion of said first compartment.

5. The humidifier of claim 4, wherein said air inlet comprises an air inlet conduit extending through said second compartment into said first compartment.

6. The humidifier of claim 5, wherein said air inlet conduit has an open upper end located at a position opposite from the location of said mixing conduit.

7. The humidifier of claim 6, wherein said second chamber is disposed between said open upper end of said inlet conduit and said mixing conduit.

8. The humidifier of claim 7, wherein said mixing conduit comprises a first tube having an open upper end in communication with said first chamber and a second tube having an upper portion connected to said second chamber and a lower portion extending within said first tube.

9. The humidifier of claim 7, wherein said heater heats said intake air as it passes through said intake conduit.

10. The humidifier of claim 1, further comprising a housing for enclosing said first and second compartments, wherein said housing comprises a removable cover for enclosing said first chamber.

11. A humidifier as defined in claim 1, wherein said first chamber surrounds said second chamber.

12. A humidifier as defined in claim 1, wherein said second chamber is located within said first chamber.

13. The humidifier as defined in claim 1, further composing an adjustable regulator fox regulating the amount of the second stream of air passing into the mixing conduit.

14. A method of delivering humidified air through an unheated conduit to a patient, said conduit having an inlet connected to a humidifier and an outlet connected to a breathing mask worn by said patient, said method comprising the steps of:
   (a) drawing intake air into from the ambient environment surrounding said humidifier by the operation of a fan located within said humidifier;
   (b) heating a first volume of the intake air in said humidifier to form a supply of heated dry air;
   (c) heating a volume of water in said humidifier and passing a second volume of the intake air over the surface of said water to form a supply of heated moisture-laden air;
   (d) mixing said heated dry air and said moisture-laden air together in said humidifier to form a stream of heated humidified air;
   (e) conveying said heated humidified air from said humidifier through said conduit to said mask, wherein the temperature and humidity of said humidified air are sufficient to substantially prevent condensation of said humidified air in said conduit.

15. The method of claim 14, wherein the temperature of said humidified air while resident within said conduit decreases to less than 40° C. and the relative humidity of said humidified air while resident within said conduit increases to greater than 80%.

16. The method of claim 15, wherein the temperature of said humidified air at said conduit inlet is within the range of 45–57° C. and the relative humidity of said humidified air at said conduit inlet is within the range of 25–55%.

17. The method of claim 16, wherein the temperature of said humidified air at said conduit outlet is within the range of 30–35° C. and the relative humidity of said humidified air at said conduit outlet is greater than 90%.

18. The method of claim 14, wherein said first and second volumes of air are heated to approximately the same temperature.

19. The method of claim 14, wherein said first and second volumes of air are heated within said humidifier to a temperature within the range of 65–80° C.

20. A method of treating inflammation of the mucous membranes of the upper respiratory tract of a patient during a treatment period comprising multiple treatment sessions comprising:
- (a) providing a portable humidifier apparatus, said apparatus comprising a source of heated humidified air, a face mask and an air delivery tube for delivering said heated humidified air from said humidifier to said face mask;
- (b) fitting said face mask over at least the nose of said patient;
- (c) delivering said heated humidified air from said humidifier to said face mask for a prolonged period of time during said treatment sessions while said patient is at rest, wherein said humidified air at said face mask is at a temperature within the range of 25–35° C. and at a relative humidity exceeding 90%; and
- (d) rinsing the sinuses of said patient at intervals between said treatment sessions with an isotonic saline solution.

21. The method as defined in claim 20, wherein each of said treatment sessions is at least four hours in length.

22. The method as defined in claim 20, wherein said portable humidifier apparatus comprises a fan for producing said source of heated humidified air.

23. The method as defined in claim 22, further comprising the steps of drawing intake air from the ambient environment surrounding said portable humidifier apparatus and heating and humidiating said air intake air to produce said source of heated humidified air.

* * * * *